United States Patent [19]

VandenBerg

[11] Patent Number: Plant 6,901

[45] Date of Patent: Jul. 4, 1989

[54] CHRYSANTHEMUM PLANT NAMED QUERNO

[75] Inventor: Cornelis P. VandenBerg, Salinas, Calif.

[73] Assignee: Yoder Brothers, Inc., Ashtabula, Ohio

[21] Appl. No.: 187,578

[22] Filed: Apr. 28, 1988

[51] Int. Cl.[4] ..... A01H 5/00

[52] U.S. Cl. ..... Plt./74

[58] Field of Search ..... Plt./74

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A chrysanthemum plant named Querno particularly characterized by its flat capitulum form; daisy capitulum type; coral-pink ray floret color; diameter across face of capitulum of up to 65 cm at maturity; uniform nine week photoperiodic flowering response to short days; peduncle length ranging from 13 to 20 mm on open, terminal sprays; and medium plant height when grown as a single stem spray cut mum.

3 Drawing Sheets

The present invention comprises a new and distinct cultivar of Chrysanthemum, botanically known as *Dendranthema grandiflora,* and referred to by the cultivar name Querno.

Querno, identified as 84237005, was originated from a cross made by Cornelis P. VandenBerg in a controlled breeding program in Salinas, Calif. in 1984.

The female parent and the male parent of Querno were both unnamed seedlings, identified respectively as 80520003 and 82J78001.

Querno was discovered and selected as one flowering plant within the progeny of the stated cross by Cornelis P. VandenBerg in December 1984 in a controlled environment in Salinas, Calif.

The first act of asexual reproduction of Querno was accomplished when vegetative cuttings were taken from the initial selection in February 1985 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Querno are firmly fixed and are retained through successive generations of asexual reproduction.

Querno has not been observed under all possible environmental conditions. The phenotype may vary significantly with variations in environment such as temperature, light intensity, and daylength.

The following observations, measurements and comparisons describe plants grown in Salinas, Calif. under greenhouse conditions which approximate those generally used in commercial greenhouse practice.

The following traits have been repeatedly observed and are determined to be basic characteristics of Querno, which, in combination, distinguish this Chrysanthemum as a new and distinct cultivar:

1. Flat capitulum form.
2. Daisy capitulum type.
3. Coral-pink ray floret color.
4. Diameter across face of capitulum up to 65 mm at maturity.
5. Uniform nine week photoperiodic flowering response to short days.
6. Peduncle length ranging from 13 to 20 cm on open terminal sprays.

7. Medium plant height, requiring 1 to 2 long day weeks prior to short days to attain a flowered plant height of 90 to 100 cm for year-round flowerings.

The accompanying photographic drawings show typical inflorescence and leaf characteristics of Querno, with the colors being as nearly true as possible with illustrations of this type.

Sheet 1 is a color photograph of Querno grown as a single stem cut spray mum.

Sheet 2 is a black and white photograph of three views of the inflorescence of Querno.

Sheet 3 is a black and white photograph showing the upper and under sides of the leaves of Querno at three stages of development (mature, intermediate and immature).

The combination of a small flower and soft coral-pink ray floret color is not represented in commercial cut mum cultivars known to the inventor. In comparison, the most similar to Querno is Pink Marble. Reference is made to Chart A, which compares certain characteristics of Querno to the same characteristics of Pink Marble. Similar traits are capitulum form and type, plant height and flowering response. The spray formation of Querno is more upright, the peduncle length is shorter and the diameter of capitulum is smaller than Pink Marble.

In the following description, color references are made to The Royal Horticultural Society Colour Chart. The color values were determined on plant material grown in Salinas, Calif. on Oct. 12, 1987.

Classification:

*Botanical.*—*Dendranthema grandiflora,* cv Querno.

*Commercial.*—Daisy cut spray mum.

INFLORESCENCE

A. Capitulum:

*Form.*—Flat.

*Type.*—Daisy.

*Diameter across face.*—Up to 65 mm at maturity.

B. Corolla of ray florets:

*Color (general tonality from a distance of three meters).*—Coral-pink.

*Color (upper surface).*—49C fading to 49D.

*Color (under surface).*—Closest to 36D.

*Shape.*—Flat, oblong. Cross section of ray straight. Longitudinal axis, straight.

C. Corolla of disc florets:

*Color (mature).*—Closest to 12A to 12B.

*Color (immature).*—Closest to 144A to 144B.

D. Reproductive organs:

*Androecium.*—Present on disc florets only; moderate pollen.

*Gynoecium.*—Present on both ray and disc florets.

PLANT

A. General Appearance:

*Height.*—Medium; 90 to 100 cm as a single stem cut mum with 1 to 2 long day weeks prior to short days.

B. Foliage:

*Color (upper surface).*—147A.

*Color (under surface).*—147B.

*Shape.*—Deeply lobed and serrated.

CHART A

COMPARISON OF QUERNO AND PINK MARBLE

| | Querno | Pink Marble |
|---|---|---|
| Ray floret color | Coral pink | Purple |
| Capitulum form and type | Flat Daisy | Flat Daisy |
| Spray formation | Upright terminal 13 to 20 cm peduncles | Semi-upright terminal to compound 20 to 25 cm peduncles |
| Diameter across face of capitulum | Up to 65 mm | Up to 83 mm |
| Plant height | Medium | Medium |
| Flowering response period | 9 weeks | 9 weeks |

COMPARISONS MADE OF PLANTS GROWN AS SINGLE STEM SPRAY CUT MUMS IN SALINAS, CALIFORNIA

I claim:

1. A new and distinct Chrysanthemum plant named Querno, as described and illustrated, and parts thereof.

* * * * *

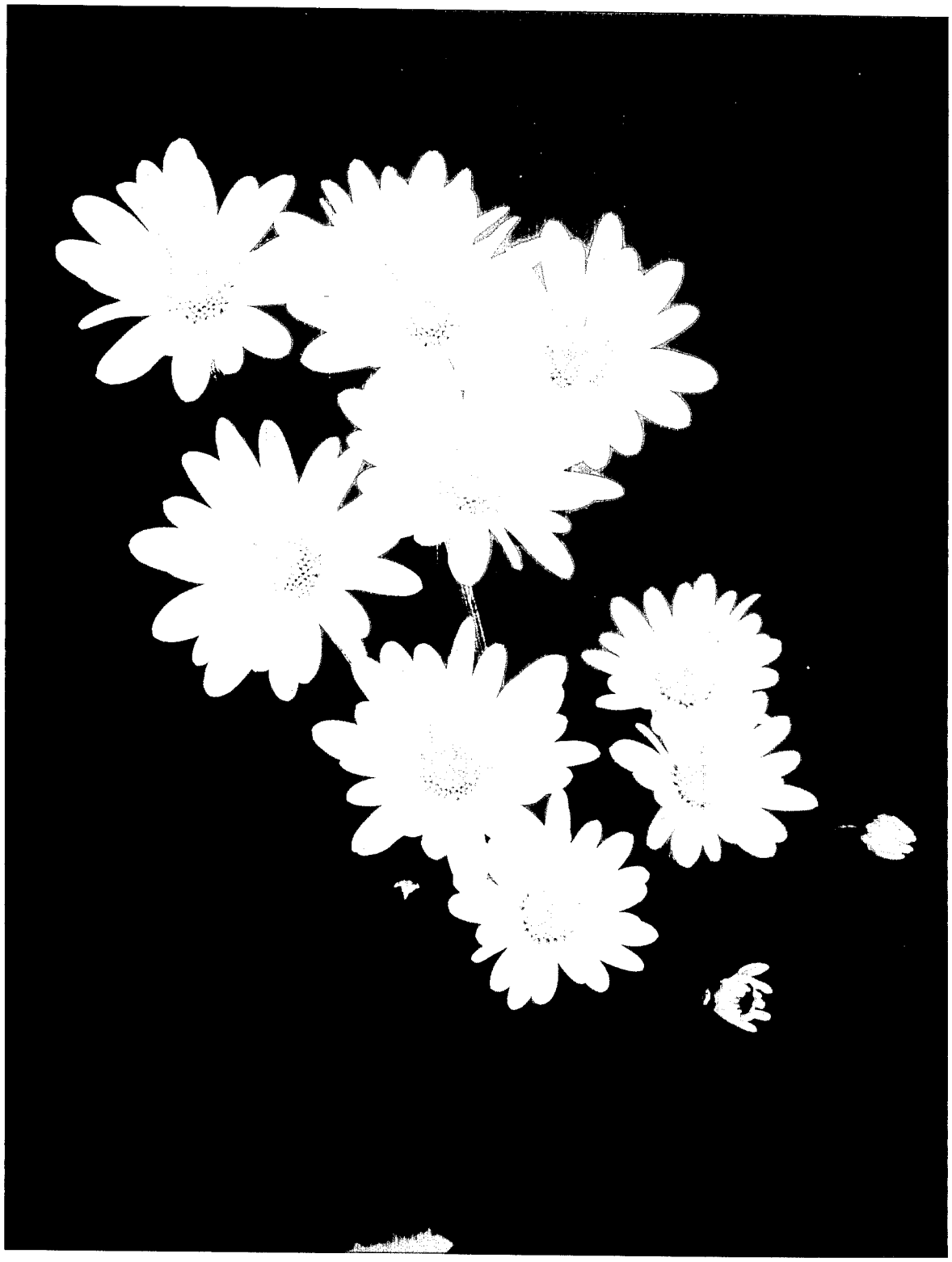

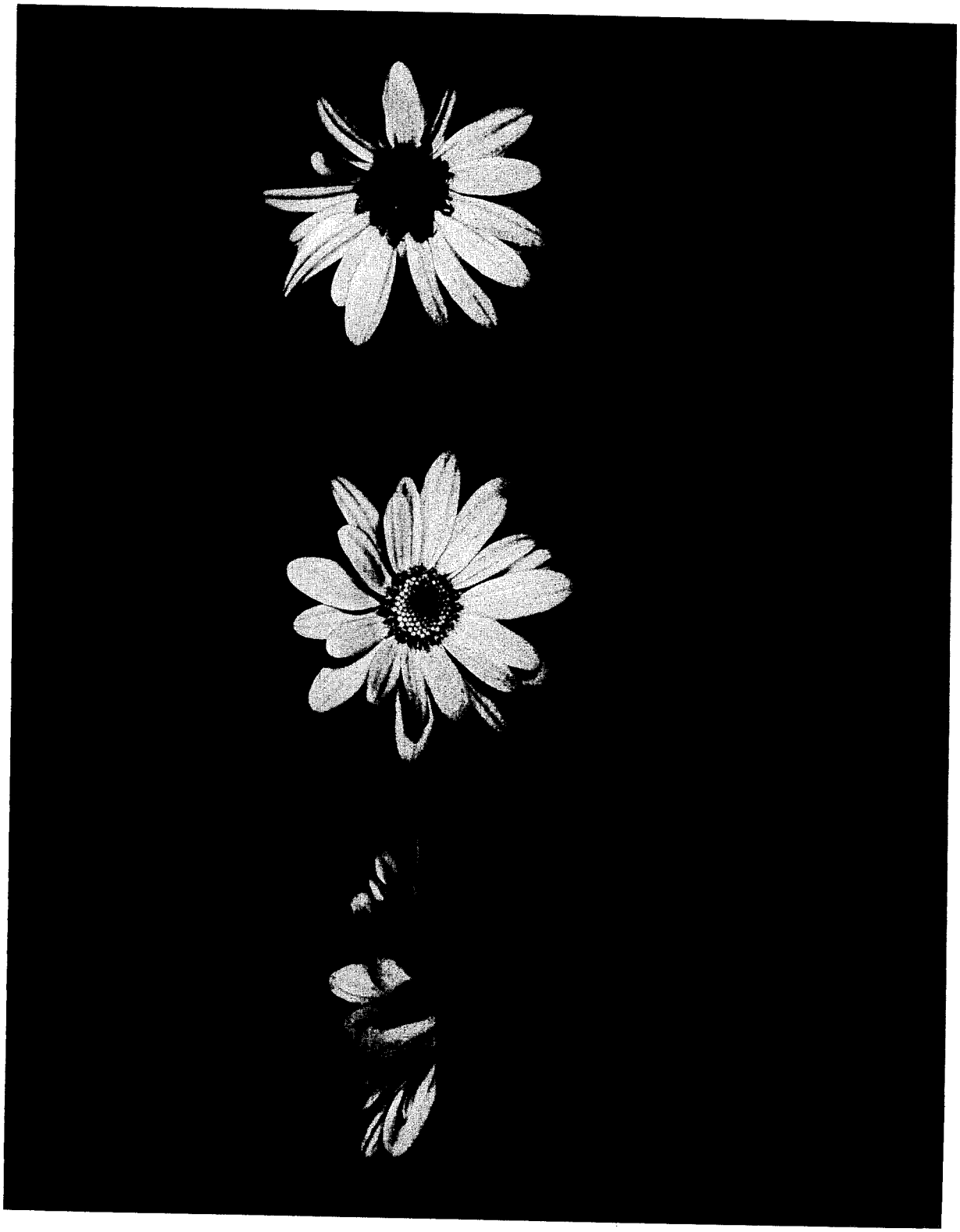

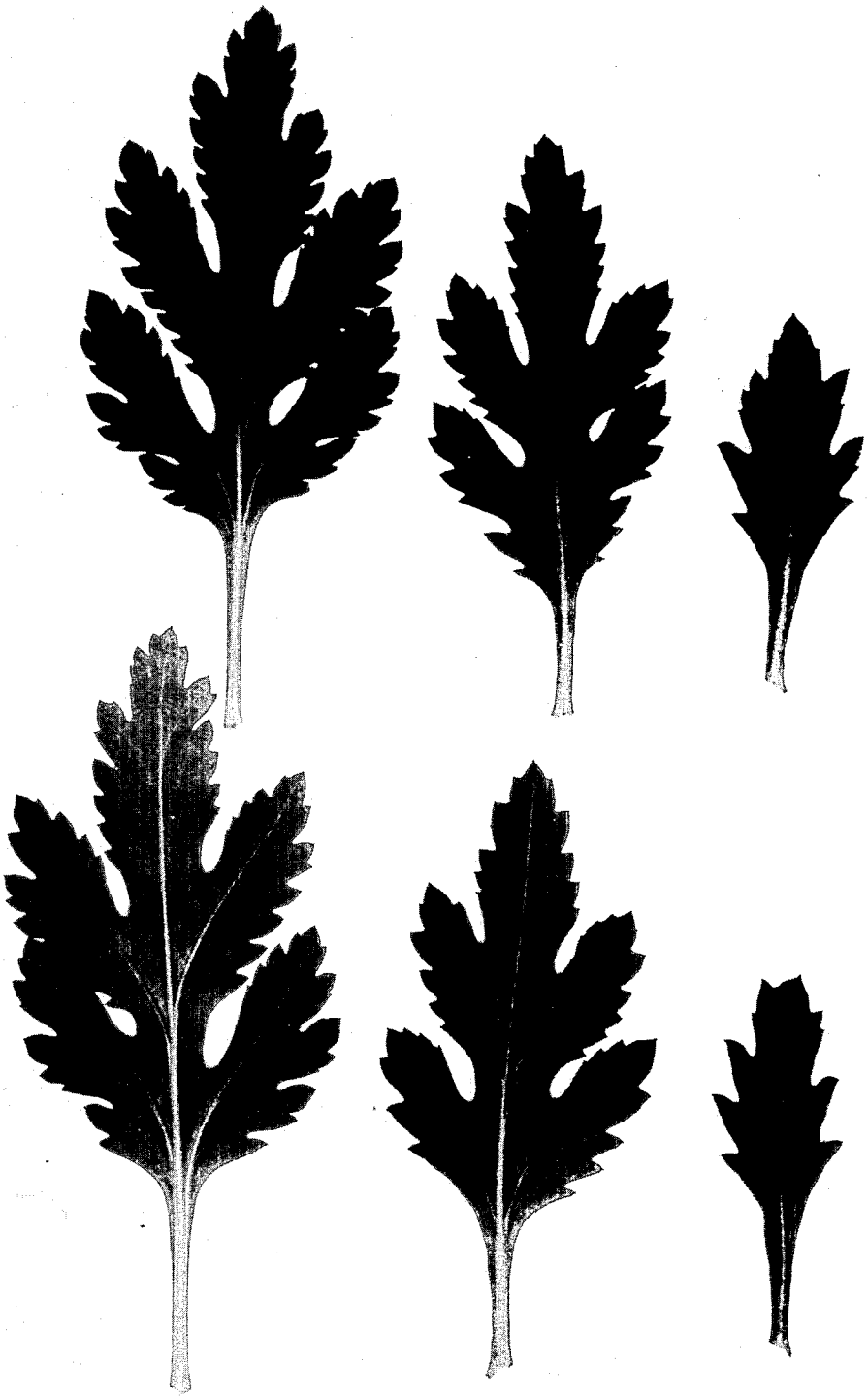

UNITED STATES PATENT AND TRADEMARK OFFICE

CERTIFICATE OF CORRECTION

PATENT NO. : Plant 6,901

DATED : July 4, 1989

INVENTOR(S) : Cornelis P. VandenBerg

It is certified that error appears in the above—identified patent and that said Letters Patent is hereby corrected as shown below:

Title page:

In line 4 of the Abstract, "65 cm" should be --65 mm--.

In line 6 of the Abstract, "13 to 20 mm" should be --13 to 20 cm--.

Signed and Sealed this

Ninth Day of April, 1991

*Attest:*

HARRY F. MANBECK, JR.

*Attesting Officer*

*Commissioner of Patents and Trademarks*